United States Patent
Li

(10) Patent No.: US 9,248,010 B2
(45) Date of Patent: Feb. 2, 2016

(54) TENSION-ADJUSTABLE SURGICAL SLING ASSEMBLY

(75) Inventor: Jamie Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2622 days.

(21) Appl. No.: 11/182,268

(22) Filed: Jul. 15, 2005

(65) Prior Publication Data

US 2007/0015957 A1    Jan. 18, 2007

(51) Int. Cl.
*A61F 2/00* (2006.01)

(52) U.S. Cl.
CPC ....... *A61F 2/0045* (2013.01); *A61F 2210/0004* (2013.01); *A61F 2250/0031* (2013.01); *A61F 2250/0067* (2013.01)

(58) Field of Classification Search
CPC .................. A61F 2/0004; A61F 2/0031–2/45; A61F 2/0063; A61F 2/0077; A61F 2002/0063–2002/009; A61F 2/0045; A61F 2/0022
USPC ........................ 600/37, 29–31; 606/139–158; 623/11.11–15.12, 23.64–23.76
See application file for complete search history.

(56) References Cited

U.S. PATENT DOCUMENTS

| | | | |
|---|---|---|---|
| 3,557,795 A * | 1/1971 | Hirsch ........................... | 606/228 |
| 4,400,833 A | 8/1983 | Kurland | |
| 4,750,492 A | 6/1988 | Jacobs | |
| 5,385,606 A * | 1/1995 | Kowanko .................. | 106/156.3 |
| 5,919,232 A | 7/1999 | Chaffringeon et al. | |
| 6,110,101 A | 8/2000 | Tihon et al. | |
| 6,273,852 B1 | 8/2001 | Lehe et al. | |
| 6,306,079 B1 * | 10/2001 | Trabucco ........................ | 600/30 |
| 6,319,264 B1 * | 11/2001 | Tormala et al. ............... | 606/151 |
| 6,582,443 B2 * | 6/2003 | Cabak et al. .................. | 606/151 |
| 6,599,318 B1 * | 7/2003 | Gabbay ....................... | 623/11.11 |
| 6,638,211 B2 | 10/2003 | Suslian et al. | |
| 6,648,921 B2 | 11/2003 | Anderson et al. | |
| 6,666,817 B2 | 12/2003 | Li | |
| 6,685,629 B2 | 2/2004 | Therin | |
| 6,689,047 B2 | 2/2004 | Gellman | |
| 6,736,823 B2 | 5/2004 | Darois et al. | |
| 6,755,781 B2 | 6/2004 | Gellman | |
| 6,911,003 B2 | 6/2005 | Anderson et al. | |
| 7,083,637 B1 * | 8/2006 | Tannhauser ................... | 606/228 |
| 2002/0028980 A1 * | 3/2002 | Thierfelder et al. ............ | 600/37 |
| 2002/0099259 A1 * | 7/2002 | Anderson et al. .............. | 600/29 |
| 2003/0050530 A1 * | 3/2003 | Neisz et al. ..................... | 600/29 |

(Continued)

FOREIGN PATENT DOCUMENTS

| | | |
|---|---|---|
| WO | WO98/35632 | 8/1998 |
| WO | WO02/19945 | 3/2002 |

(Continued)

OTHER PUBLICATIONS

Kafali et al., "A New Tension-Adjustment Technique for Sling Operation: An Animal Model," Urologia Internationalis, 72:58-61, (2004).

(Continued)

*Primary Examiner* — Catherine B Kuhlman

(57) ABSTRACT

The invention provides, in one embodiment, a sling assembly including two separate slings or sling sections connected via a removable or biodegradable connection mechanism such that the tension in the sling assembly can be readily adjusted after the sling assembly is surgically implanted.

7 Claims, 5 Drawing Sheets

(56) References Cited

U.S. PATENT DOCUMENTS

| | | |
|---|---|---|
| 2003/0065402 A1* | 4/2003 | Anderson et al. .......... 623/23.66 |
| 2003/0191480 A1 | 10/2003 | Ulmsten et al. |
| 2003/0191537 A1* | 10/2003 | Wasielewski .............. 623/22.11 |
| 2004/0006353 A1* | 1/2004 | Bosley et al. ................ 606/151 |
| 2004/0039246 A1* | 2/2004 | Gellman et al. ................ 600/30 |
| 2004/0132365 A1 | 7/2004 | Therin et al. |
| 2004/0144395 A1* | 7/2004 | Evans et al. ................... 128/885 |
| 2004/0231678 A1 | 11/2004 | Fierro |
| 2004/0249240 A1 | 12/2004 | Goldmann et al. |
| 2005/0027160 A1 | 2/2005 | Siegel et al. |
| 2005/0038452 A1 | 2/2005 | Chu |
| 2005/0070829 A1 | 3/2005 | Therin et al. |
| 2005/0080317 A1* | 4/2005 | Merade ........................... 600/30 |
| 2005/0240261 A1* | 10/2005 | Rakos et al. ................. 623/1.51 |
| 2005/0267325 A1* | 12/2005 | Bouchier et al. ................ 600/37 |
| 2006/0264698 A1* | 11/2006 | Kondonis et al. .............. 600/37 |

FOREIGN PATENT DOCUMENTS

| | | | |
|---|---|---|---|
| WO | WO 03/002027 | 1/2003 | |
| WO | WO 03086205 A2 * | 10/2003 | ............. A61B 17/04 |
| WO | WO2004/043294 | 5/2004 | |

OTHER PUBLICATIONS

Hakim, et al., "Use of Biodegradable Mesh as a Transport for a Cultured Uroepithelial Graft: An Improved Method Using Collagen Gel," Urology, vol. 44, No. 1, (1994).

Matapurkar, et al., "A New Technique of 'Marlex®-Peritoneal Sandwich' in the Repair of Large Incisional Hernias," World J. Surg., vol. 15, pp: 768-770 (1991).

Olsen, et al., "Urethral Reconstruction With a New Synthetic Absorbable Device," Scand. J. Urol. Nephrol. vol. 26, pp. 323-326 (1992).

* cited by examiner

TENSION-ADJUSTABLE SURGICAL SLING ASSEMBLY

TECHNICAL FIELD

The invention generally relates to surgical sling assemblies, and related methods, for providing anatomical support in a patient's body. More particularly, in various embodiments, the invention relates to a surgical sling formed from two separate and distinct sling sections connected via a removable and/or biodegradable connection mechanism.

BACKGROUND INFORMATION

Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results.

A popular treatment of SUI involves implanting a supportive sling under a patient's bladder neck or mid-urethra to provide a urethral platform. Placement of the surgical sling limits the endopelvic fascia drop while providing compression to the urethral sphincter to improve coaptation. Typically, a protective sleeve encloses the sling during the placement procedure. Once the surgical sling assembly, which includes the sling and the sleeve, is correctly positioned in the patient's periurethral tissues, the sleeve is physically removed from about or slid off the sling and withdrawn from the patient's body, leaving behind only the sling in the patient's tissues.

Proper tension of a sling is critical for the sling to achieve its intended functions. If the sling is too loosely associated with its intended physiological environment, it may be ineffective in supporting the urethra and treating incontinence. If the sling is too tightly placed, several complications can arise, including urine retention, erosion and/or severing of the urethra or other damage to surrounding tissue. Additionally, even when a sling is placed with the appropriate amount of the tension, a patient's body may undergo changes, such as weight gain, that may cause over-tensioning. Therefore, it is sometimes necessary to modify the sling tension subsequent to the sling placement.

Accordingly, improved surgical slings for which tension can be readily adjusted subsequent to implantation are needed for better treatment of SUI.

SUMMARY OF THE INVENTION

The invention addresses the deficiencies in the prior art by, in one embodiment, providing an implantable tension-adjustable surgical sling assembly and related methods, for providing anatomical support in the periurethral tissue of a patient's body (e.g., for providing a urethral platform). The surgical sling assembly includes two separate sling sections connected via a removable or biodegradable connection mechanism. After the sling is surgically placed into the body, the connection mechanism connecting the two separate sling sections is either removed or dissolved after a period of time, during which time sufficient scar tissue for supporting the urethra from below has formed if the connecting mechanism is underneath the urethra. If the connecting mechanism is on the side of the urethra instead of underneath, the developed scar tissue will hold the two sling sections together. Thereafter, the two separate slings, together with the scar tissue formed between them, continue to provide the requisite support for the urethra for maintaining continence. The scar tissue naturally responds to changes in the surrounding environment that would have otherwise caused the tension in the sling to be too great or too little. As a result, the tension in the sling naturally and automatically adjusts.

According to one aspect, a sling assembly, according to the invention, includes first and second separate and distinct sling sections, each sling section includes first and second terminal ends. In one configuration, the second terminal end of the first sling section attaches to the first terminal end of the second sling section to form an elongated sling sized and shaped for supporting the urethra and/or the bladder neck in a patient to ameliorate urinary incontinence. In some embodiments, the two sling sections are attached via a biodegradable material. However, in other embodiments, the material for connecting the two slings sections is non-biodegradable but may be cut and/or otherwise removed subsequent to sling implantation.

According to one configuration, the second terminal end of the first sling section overlaps with the second terminal end of the second sling section and the overlapped portion is bonded together, for example, by way of gluing and/or heat bonding. According to one embodiment, the overlapping portions of the first and second sling sections are biodegradable. Thus, over a period of time subsequent to implantation, the overlapping portions dissolve or are otherwise absorbed into the body of the patient, leaving two separate and distinct sling sections in the body. According to one feature, the biodegradable materials for the overlapping portions are selected such that tissue in-growth occurs prior to the overlapping portions dissolving into the body of the patient. The tissue in-growth forms scar tissue, which provides a natural sling material and hold the two sling sections together. In one configuration, the biodegradable material of the overlapping portions are selected such that they do not fully dissolve until scar tissue has formed along the overlapped area. The scar tissue that remains after the overlapping section dissolves provides a natural connection between the first and second sling sections. This natural connection is capable of expanding and/or contracting in response to changes in the patient's body, such as, due to weight gain or other change in the patient's anatomy. According to another feature, the overlapping biodegradable sections of the first and second sling assembly may be treated, for example, with an agent that promotes organized scar tissue formation.

According to another configuration, the second end of the first sling section and the first end of the second sling section are connected via an interwoven filament. According to one embodiment, the interwoven filament connects the second end of the first sling section and the first end of the second sling section such that they are adjacent to and in contact with each other but not substantially overlapping. The interwoven filament may, in various embodiments, be biodegradable, as in the case of the overlapping midsection. According to other embodiments, the filament may be non-biodegradable, but removable by a medical operator subsequent to sling implantation and sufficient scar tissue in-growth. In another embodiment, the second end of the first sling section and the second end of the first sling section are interconnected by way of an interwoven rod. The rod preferably spans the width of the first and second sling sections at the location of interconnection, and, as in the case of the filament, the rod may be biodegradable. However, in other embodiments, the rod may be configured to be removed by a medical operator subsequent to sufficient scar tissue in-growth. In a further embodiment, the second end of the first sling section and the first end of the second sling section overlap and are clipped together. As in the case of the interconnecting rod and the interwoven filament, the connector may be configured either for biodegradation or for subsequent removal by a medical operator. The clip may be sized and shaped for contacting an upper surface of either the first or second sling sections and a lower surface of the other sling section to clip the two sling sections together with the sling sections sandwiched therebetween. In one configuration, the portion of the clip that contacts the upper sling surface may be sized/calibrated to provide a particular gap between the urethra and the upper sling surface for initial tensioning purposes. In another configuration, the clip is located beneath the sling and contacts the lower surface of the first sling section and the lower surface of the second sling section and sandwiches the upper surfaces of the ends of the first and second sling sections together. In this configuration, the clip may be also employed as a tab for assisting the initial placement of the sling assembly. According to another configuration, the second end of the first sling section and the first end of the second sling section are connected via staples. According to a further configuration, the second end of the first sling section and the first end of the second sling section are connected via rivets or eyelet rivets.

According to a further configuration, either the entire length of the first and second sling sections or at least a portion that include the second end of the first sling section and the first end of the second sling sections is sandwiched between two biodegradable layers to form an elongated sling assembly sized and shaped for supporting the urethra and/or the bladder neck in a patient to ameliorate urinary incontinence. In one embodiment, either the entire length of the first and second sling sections or at least a portion that include the second end of the first sling section and the first end of the second sling sections is wrapped around with a biodegradable layer.

According to a further configuration, the biodegradable connection mechanism and/or the sling may include a bioactive agent for release into the patient's tissue after implantation. The bioactive agent can be a drug or a tissue growth factor that stimulates host scar tissue formation.

The foregoing and other objects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION OF ILLUSTRATIVE EMBODIMENTS

The invention addresses the deficiencies in the prior art by, in various embodiments, providing systems, methods, and devices relating to an implantable surgical sling assembly that is tension adjustable subsequent to being implanted at an anatomical location in the body of a patient. In particular embodiments, the sling assembly of the invention is sized and shaped for providing a urethral platform for treating urinary incontinence in a patient.

The term "biodegradable", as used herein, refers to the property of a material that dissolves in the body. Such material may also be absorbed into the body, i.e., bioabsorbable.

Figure 1:
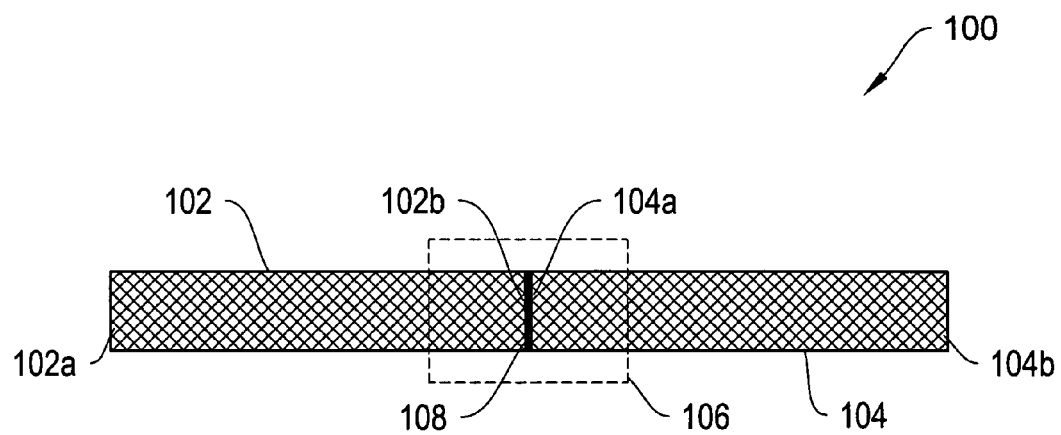
FIG. 1 is a top view of a sling assembly including two separate and distinct sling sections which are connected in a middle region via a removable and/or biodegradable connection mechanism according to an illustrative embodiment of the invention.

FIG. 1 shows a top view of a sling assembly 100, according to one illustrative embodiment of the invention, that includes two separate and distinct sling sections, 102 and 104. The sling section 102 includes first terminal end 102a and second terminal end 102b. The sling section 104 includes first terminal end 104a and second terminal end 104b. In the illustrative configuration depicted in FIG. 1, the second terminal end 102b of the first sling section 102 attaches to the first terminal end 104a of the second sling section 104 at the location of interconnection 108 to form an elongated sling assembly 100 sized and shaped for supporting the urethra and/or the bladder neck in a patient to ameliorate urinary incontinence.

In the illustrative configuration of FIG. 1, the two sling sections 102 and 104 are of equal length and the interconnection 108 is therefore in the middle of the sling assembly 100. However, this needs not to be the case. In alternative embodiments, the two sling sections 102 and 104 are of unequal length and the interconnection 108 may therefore not be in the middle of the sling assembly 100.

In some embodiments, the two sling sections 102 and 104 are attached via a biodegradable and/or bioabsorbable material. However, in other embodiments, the material for connecting the two slings sections 102 and 104 is non-biodegradable but may be cut and/or otherwise removed subsequent to sling implantation and sufficient scar tissue in-growth. The non-biodegradable material may be labeled with a marker/tracer such that a medical operator can readily locate the position of the material to be removed via X-ray or other detection methods. For example, the non-biodegradable material may be radio-opaque and/or of a contrasting color to the body tissue to allow for visualization.

Although FIG. 1 depicts a sling assembly 100 with two separate and distinct sling sections 102 and 104, this needs not be the case. For example, a sling assembly 100 may contain 3, 4, 5, 6 or more separate and distinct sling sections, with each sling section connected to its neighboring sling section via any of the approaches disclosed herein. In some embodiments, each sling section is attached to its neighboring sling section via a biodegradable and/or bioabsorbable material. However, in other embodiments, the material for connecting the slings sections is non-biodegradable but may be cut and/or otherwise removed subsequent to sling implantation and sufficient scar tissue in-growth.

Figure 2A:
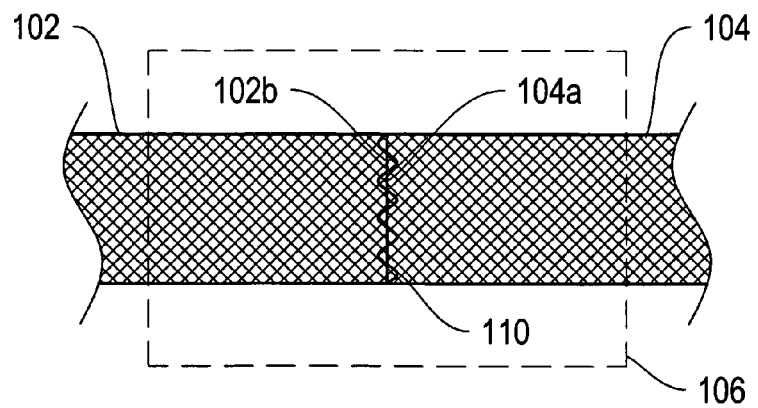
FIG. 2A is a top view of a middle region of a sling assembly such as depicted in FIG. 1, with the sling sections connected via one or more filaments according to an illustrative embodiment of the invention.

FIG. 2A shows a top view of the middle region 106 of a sling assembly such as depicted in FIG. 1 in which the sling sections 102 and 104 are connected at the location of interconnection 108 via one or more interwoven filaments 110 according to an illustrative embodiment of the invention. According to one embodiment, the interwoven filament 110 connects the second terminal end 102b of the first sling section 102 and the first terminal end 104a of the second sling section 104 such that they are adjacent to and in contact with each other but not substantially overlapping. The interwoven filament 110 may, in various embodiments, be single stranded or multi-stranded. According to further embodiments, the interwoven filament 110 may be biodegradable/and or bioabsorbable. Thus, over a period of time subsequent to implantation, the interwoven filament 110 dissolves or is otherwise absorbed into the body of the patient, leaving two separate and distinct sling sections in the body. According to other embodiments, the filament 110 may be non-biodegradable, but may be cut or otherwise removed by a medical operator subsequent to sling implantation and sufficient scar tissue in-growth. The non-biodegradable material may be labeled with a marker/tracer such that a medical operator can readily locate the position of the material to be removed via X-ray or other detection methods. After the interwoven filament 110 dissolves or is removed, the first the second sling sections 102 and 104 are no longer attached to each other and can move towards or away from each other in response to changes in the patient's body, such as, for example, due to weight gain or change in the patient's anatomy. According to another feature, the interwoven filament 110 may be treated, for example, with an agent that promotes organized scar tissue formation.

Figure 2B:
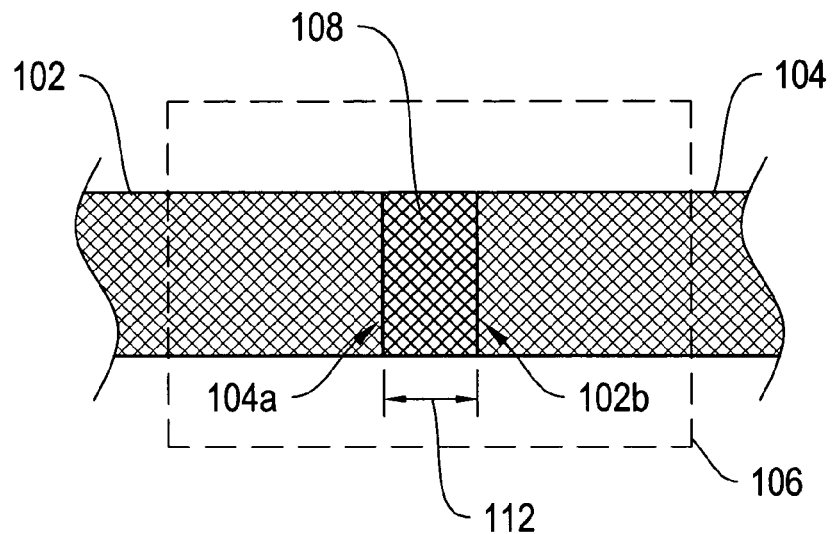
FIG. 2B is a top view of a middle region of a sling assembly such as depicted in FIG. 1, with the sling sections connected via a bonding mechanism according to another illustrative embodiment of the invention.

FIG. 2B is a top view of the middle region 106 of a sling assembly such as depicted in FIG. 1 in which the sling sections 102 and 104 are connected at the location of interconnection 108 via a bonding mechanism according to an illustrative embodiment of the invention. According to one configuration as depicted in FIG. 2B, the second terminal end 102b of the first sling section 102 overlaps and in contact with the first terminal end 104b of the second sling section 104 at the location of interconnection 108. The overlapped portions are bonded together via a bonding mechanism. According to one embodiment, the bonding mechanism is biodegradable/bioabsorbable, and the overlapping portions of the first 102 and second 104 sling sections are non-biodegradable. Thus, over a period of time subsequent to implantation, the bonding mechanism dissolves, leaving two separate and distinct sling sections 102 and 104 in the body. Because the two sling sections 102 and 104 are no longer bonded together, they may move toward or away from each other in response to changes in the patient's anatomy. According to another embodiment, the overlapped portions of the first and second sling sections 102 and 104 are bonded together via a bonding mechanism, such as, for example, glue or heat bonding, and the overlapping portions of the first and second sling sections are biodegradable/bioabsorbable. Thus, over a period of time subsequent to implantation, the overlapping portions dissolve or otherwise being absorbed into the body of the patient, leaving two separate and distinct sling sections in the body. According to another feature, the overlapping biodegradable/bioabsorbable portions of the first and second sling sections 102 and 104 may be treated, for example, with an agent that promotes organized scar tissue formation.

Figure 2C:
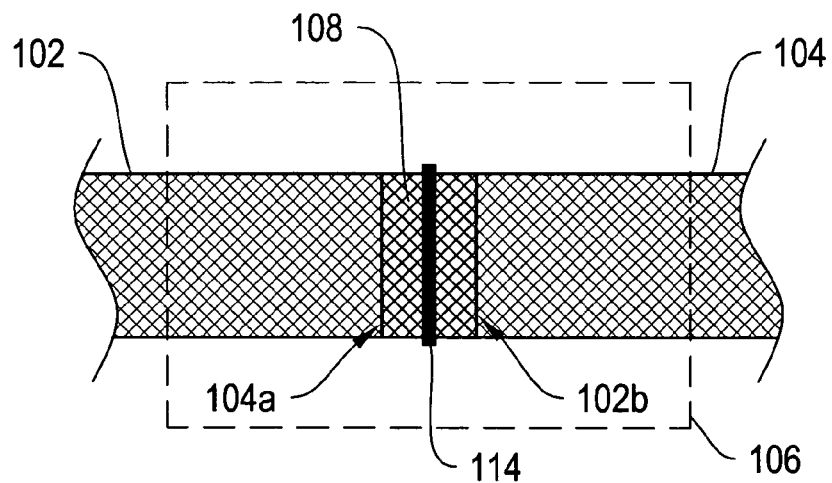
FIG. 2C is a top view of a middle region of a sling assembly such as depicted in FIG. 1, with the sling sections connected via a rod interfitted into the mesh of the slings according to another illustrative embodiment of the invention.

FIG. 2C shows a top view of the middle region 106 of a sling assembly, such as depicted in FIG. 1, in which the sling sections 102 and 104 are connected at the location of interconnection 108 via an interwoven rod 114 interfitted into the mesh of the first and second sling sections 102 and 104, respectively, according to an illustrative embodiment of the invention. According to one embodiment, the interwoven rod 114 connects the second terminal end 102b of the first sling section 102 and the first terminal end 104a of the second sling section 104 such that they are adjacent to and in contact with each other but not substantially overlapping. In other configurations, the sling sections 102 and 104 overlap in the region 108. The rod 114 preferably spans the width of the first sling section 102 and second sling section 104 at the location of interconnection 108. The interwoven rod 114 may, in various embodiments, be made of different materials. In some embodiments, the rod 114 is made of biodegradable materials such as those described in more detail below. In other embodiments, the rod 114 is made of non-biodegradable materials such as, for example, plastics, metal and rubber, and are configured to be removed by a medical operator subsequent to sling implantation and sufficient scar tissue in-growth. The non-biodegradable material that makes up rod 114 may be labeled with a marker/tracer such that a medical operator can readily locate the position of the material to be removed via X-ray or other detection methods. According to another feature, the rod 114 may be treated, for example, with an agent that promotes organized scar tissue formation.

Figure 3A:
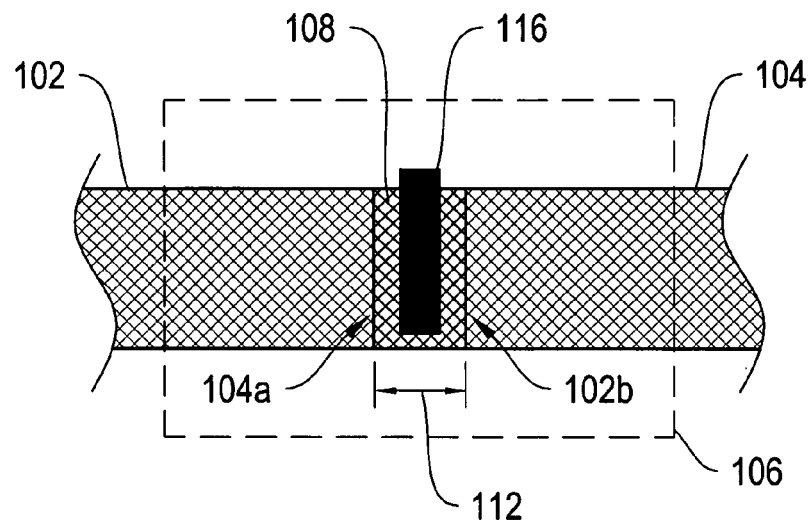
FIG. 3A is a top view of a middle region of a sling assembly such as depicted in FIG. 1, with the sling sections connected via a clip according to another illustrative embodiment of the invention.

FIG. 3A is a top view of a middle region 106 of a sling assembly, such as depicted in FIG. 1, in which the sling sections 102 and 104 are connected at the location of interconnection 108 via a clip 116 holding together the first and second sling sections 102 and 104 according to an illustrative embodiment of the invention. According to one embodiment, the clip 116 holds together the second terminal end 102b of the first sling section 102 and the first terminal end 104a of the second sling section 104 such that they overlap and are in contact with each other in the region 108. The clip 116 may span the entire or partial width of the first sling section 102 and second sling section 104 at the location of interconnection 108. The clip 116 may, in various embodiments, be made of different materials. In some embodiments, the clip 116 is made of biodegradable/bioabsorbable materials such as those described in more detail below. In other embodiments, the clip 116 is made of non-biodegradable materials such as, for example, plastics, metal and rubber, and are configured to be removed by a medical operator subsequent to sling implantation and sufficient scar tissue in-growth. The non-biodegradable material may be labeled with a marker/tracer such that a medical operator can readily locate the position of the material to be removed via X-ray or other detection methods. According to another feature, the clip 116 may be treated, for example, with an agent that promotes organized scar tissue formation.

The clip 116 may be sized and shaped for contacting the upper surface of either the first or second sling sections and a lower surface of the other sling section to clip the two sling sections together with the sling sections sandwiched therebetween. In one configuration, the portion of the clip 116 that contacts the upper sling surface may be sized/calibrated to provide a particular gap between the urethra and the sling for initial tensioning purposes.

Figure 3B:
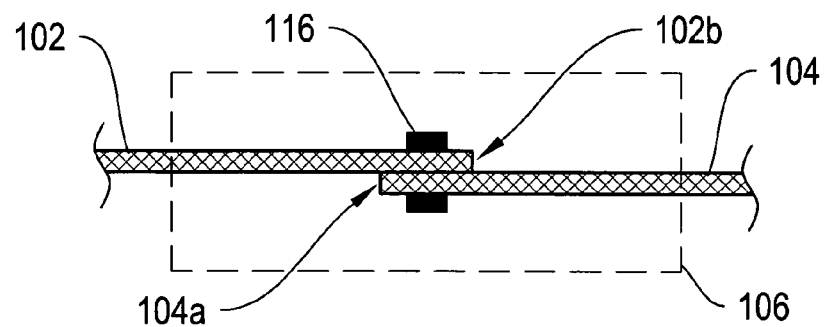
FIG. 3B is a side view of the clip and sling arrangement of FIG. 3A.

FIG. 3B is a side view of the clip and sling arrangement of FIG. 3A. As shown in FIG. 3B, the second terminal end 102b of the first sling section 102 and the first terminal end 104a of the second sling section 104 are clipped together via the clip 116 such that they overlap and are in contact with each other In addition to the configurations depicted in the figures above, any other suitable mechanism for interconnecting the two sling sections 102 and 104 may be used including, without limitation, a staple, a rivet and an eyelet rivet.

Figure 4:
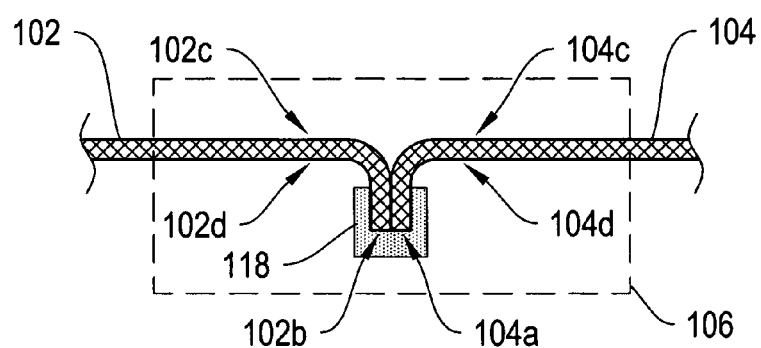
FIG. 4 is a side view of a middle region of a sling assembly such as depicted in FIG. 1, with the sling sections connected via a tab according to another illustrative embodiment of the invention.

FIG. 4 is a side view of a middle region 106 of a sling assembly such as depicted in FIG. 1, in which the sling sections 102 and 104 are connected at the location of interconnection 108 via a tab 118 according to an illustrative embodiment of the invention. As shown in FIG. 4, the tab 118 is located beneath the sling sections 102 and 104 and contacts the lower side 102d of the first sling section 102 and the lower side 104d of the second sling section 104, such that the upper side 102c of the second end 102b of the first sling section 102 and upper side 104c of the first end 104a of the second sling section 104 overlap and are in contact with each other. The tab 118 and may be also employed as a tab for assisting the initial placement of the sling assembly. The tab 118 may in various embodiments be made of different materials. In some embodiments, the tab 118 is made of biodegradable/bioabsorbable materials such as those described in more detail below. In other embodiments, the tab 118 is made of non-biodegradable materials such as, for example, plastics, metal and rubber, and are configured to be removed by a medical operator subsequent to sling implantation and sufficient scar tissue in-growth. The non-biodegradable material may be labeled with a marker/tracer such that a medical operator can readily locate the position of the material to be removed via X-ray or other detection methods. According to another feature, the tab 118 may be treated, for example, with an agent that promotes organized scar tissue formation.

Figure 5:
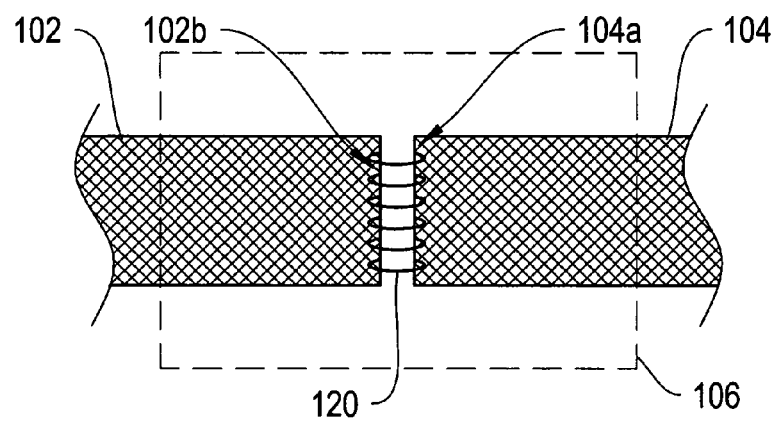
FIG. 5 is a top view of a middle region of a sling assembly such as depicted in FIG. 1, with the sling sections connected via one or more non-biodegradable filaments according to another illustrative embodiment of the invention.

FIG. 5 is a top view of a middle region 106 of a sling assembly, such as depicted in FIG. 1, in which the sling sections 102 and 104 are connected via one or more non-biodegradable filaments 120 according to an illustrative embodiment of the invention. In the configuration depicted in FIG. 5, the first sling section 102 and the second sling section 104 do not directly contact each other. The filaments 120 may in various embodiments be single stranded or multi-stranded. The filaments 120 may be configured to be cut or otherwise removed by a medical operator subsequent to sling implantation and sufficient scar tissue in-growth. The non-biodegradable material may be labeled with a marker/tracer such that a medical operator can readily locate the position of the material to be removed via X-ray or other detection methods.

According to another feature, the filaments 120 may be treated, for example, with an agent that promotes organized scar tissue formation.

Figure 6:
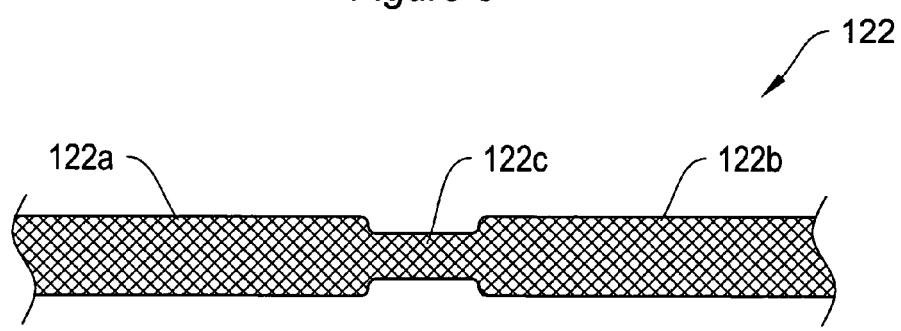
FIG. 6 is a top view of a sling having a narrower biodegradable middle portion according to another illustrative embodiment of the invention.

FIG. 6 is a top view of a sling 122 having a narrowed biodegradable/bioabsorbable middle portion according to another illustrative embodiment of the invention. In this embodiment, the sling 122 has a first end section 122a and a second end section 122b, and a biodegradable/bioabsorbable middle section 122c having a narrower width than the sling sections 122a and 122b. Preferably, the width of the section 122c is narrower than the width of sections 122a and 122b by at least about 10%, 15%, 20%, 25% or 30%. Over a period of time subsequent to implantation, the middle section 122c dissolves or is otherwise absorbed into the body of the patient, leaving two separate and distinct sling sections 122a and 122b in the body. According to another feature, the middle section 122c of the sling 122 may be treated, for example, with an agent that promotes organized scar tissue formation. According to another feature, the width of the middle section 122c is chosen based on how long it is to take for it to dissolve (e.g., the wider it is the longer it takes to dissolve.)

Figure 7A:
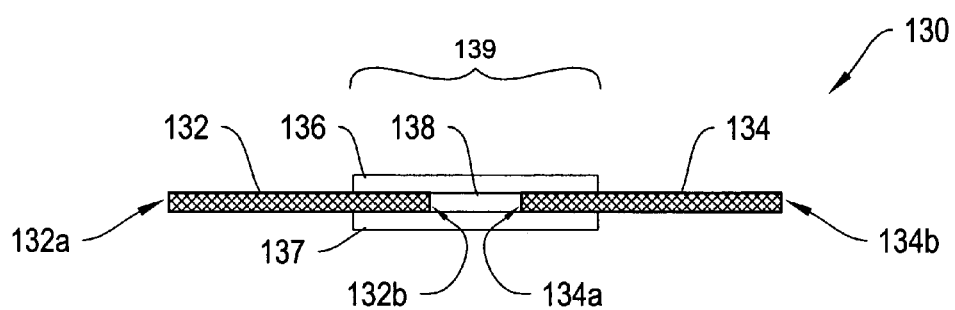
FIG. 7A depicts a side view of a sling assembly including a middle portion including a gap between two separate and distinct non-biodegradable sling section ends and the middle portion is sandwiched between two biodegradable layers.

FIG. 7A depicts a side view of a sling assembly 130 that includes two separate and distinct non-biodegradable sling sections; first sling section 132 and second sling section 134, according to an illustrative embodiment of the invention. The first sling section 132 includes first terminal end 132a and second terminal end 132b. The second sling section 134 includes first terminal end 134a and second terminal end 134b. In the illustrative configuration of FIG. 7A, the second terminal end 132b of the first sling section 132 and the first terminal end 134a of the second sling section 134 do not directly contact with each other and a gap 138 exists therebetween. The middle portion 139 of the sling assembly 130, including the gap 138, the second end 132b of the first sling section 132, and the first end 134a of the second sling section 134, is sandwiched between a first biodegradable/bioabsorbable layer 136 and a second biodegradable/bioabsorbable layer 137 to form an elongated sling assembly 130 sized and shaped for supporting the urethra and/or the bladder neck in a patient to ameliorate urinary incontinence. In alternative embodiments, rather than employing two layers 136 and 137, a single biodegradable/bioabsorbable layer wraps around the middle portion of the sling assembly. Over a period of time subsequent to implantation of the sling assembly 130 and after sufficient scar tissue in-growth, the biodegradable/bioabsorbable layers 136 and 137 dissolve or are otherwise absorbed into the body of the patient, leaving two separate and distinct sling sections 132 and 134, which can move toward or away from each other in response to changes in the patient's body, such as, for example, due to weight gain, other change in the patient's anatomy, patient movement, or muscle expansion or contraction. According to another feature, the biodegradable layers 136 and 137 may be treated, for example, with an agent that promotes organized scar tissue formation.

Figure 7B:
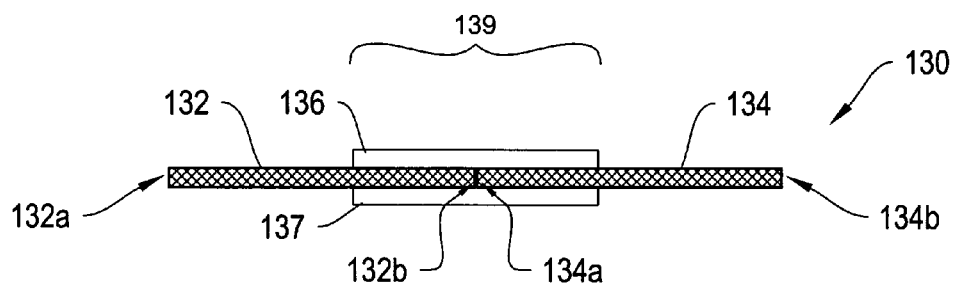
FIG. 7B depicts a side view of a sling assembly including a middle portion including two separate and distinct non-biodegradable sling section ends in contact with each other and the middle portion is sandwiched between two biodegradable layers.

FIG. 7B depicts a side view of another configuration of sling assembly 130 including two separate and distinct non-biodegradable sling sections; first sling section 132 and second sling section 134, which are in contact with each other, according to another illustrative embodiment of the invention. The middle portion 139 of the sling assembly 130, including the gap 138, the second end 132b of the first sling section 132, and the first end 134a of the second sling section 134, is sandwiched between a first biodegradable/bioabsorbable layer 136 and a second biodegradable/bioabsorbable layer 137 to form an elongated sling assembly 130 sized and shaped for supporting the urethra and/or the bladder neck in a patient to ameliorate urinary incontinence. In alternative embodiments, a biodegradable/bioabsorbable layer wraps around the middle portion of the sling assembly.

Figure 7C:
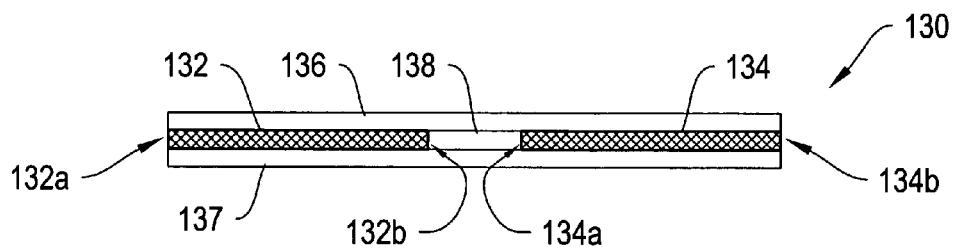
FIG. 7C depicts a side view of a sling assembly that is sandwiched between two biodegradable layers.

FIG. 7C depicts a side view of another configuration of a sling assembly 130 including two separate and distinct non-biodegradable sling sections 132 and 134, according to an illustrative embodiment of the invention. In the illustrative configuration depicted in FIG. 7C, the second terminal end 132b of the first sling section 132 and the first terminal end 134a of the second sling section 134 do not directly contact with each other and a gap 138 exists therebetween. The first and the second sling sections 132 and 134, together with the gap 138 between them, are sandwiched along their entire length between two biodegradable/bioabsorbable layers 136 and 137. In an alternative embodiment, a biodegradable/bioabsorbable layer wraps around the first and the second sling sections 132 and 134 along their entire length, including the gap 138 between them.

According to one feature, the biodegradable/bioabsorbable materials for the interwoven filament 110 as depicted in FIG. 2A, the overlapping portions in FIG. 2B, the rod 114 as depicted in FIG. 2C, the clip 116 as depicted in FIGS. 3A and 3B, the tab 118 as depicted in FIG. 4, the filaments 120 as depicted in FIG. 5, the narrower middle section 122c as depicted in FIG. 6, and the biodegradable/bioabsorbable layers 136 and 137 as depicted in FIG. 7A-C, are selected such that tissue in-growth occurs prior to the overlapping portions dissolving into the body of the patient. The tissue in-growth forms scar tissue which links the two sling sections and becomes a natural part of the sling material. The biodegradable/bioabsorbable material of the overlapping portions are selected such that they do not fully dissolve until scar tissue has formed along the overlapped area. The scar tissue that remains after the overlapping section dissolves provides a natural connection between first and second sling sections. This natural connection expands and/or contracts in response to changes in the patient's body, for example, due to weight gain, or other changes in the patient's anatomy, or movement, muscle expansion and/or muscle contraction.

Examples of biodegradable materials that may be used in the invention for the biodegradable connection mechanism and/or the sling include, without limitation, polylactic acid (PLA), polyglycolic acid (PGA), poly-L-lactic acid (PLLA), human dermis and decellularized animal tissue. Human tissues may be derived, for example, from human cadaveric or engineered human tissue. Animal tissues may be derived, for example, from porcine, ovine, bovine, and equine tissue sources. The material may be an omnidirectional material, a material that has equivalent tensile strength from any direction, such as pericardium or dermis. Alternatively, the material may be an oriented material, a material that has a single direction where the tensile strength of the material is the highest. Oriented materials may include rectus fascia and/or facia lata.

Additionally, exemplary biodegradable polymers, which may be employed for the biodegradable connection mechanism and/or the sling, in addition to those listed above, include, but are not limited to, polylactic acid, polyglycolic acid and copolymers and mixtures thereof, such as poly(L-lactide) (PLLA), poly(D,L-lactide) (PLA), polyglycolic acid [polyglycolide (PGA)], poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), poly(D,L-lactide-co-caprolactone) (PLA/PCL), and poly(glycolide-co-caprolactone) (PGA/PCL); polyethylene oxide (PEO); polydioxanone (PDS); polypropylene fumarate; polydepsipeptides, poly(ethyl glutamate-co-glutamic acid), poly(tert-butyloxy-carbonylmethyl glutamate); polycaprolactone (PCL), poly(hydroxy butyrate), polycaprolactone co-butylacrylate, polyhydroxybutyrate (PHBT) and copolymers of polyhydroxybutyrate; polyphosphazenes, poly(phosphate ester); maleic anhydride copolymers, polyiminocarbonates, poly[(97.5% dimethyl-trimethylene carbonate)-co-(2.5% trimethylene carbonate)], cyanoacrylate, hydroxypropylmethylcellulose; polysaccharides, such as hyaluronic acid, chitosan and regenerate cellulose; poly(amino acid) and proteins, such as gelatin and collagen; and mixtures and copolymers thereof.

Illustrative slings used with the invention may be between about 10 cm to about 45 cm in length and about 0.5 cm to about 5.5 cm in width, though the length, width and shape of the sling can be selected for the body part of the patient that requires support. By way of example, in some embodiments, the sling is about 45 cm in length and about 1.1 cm in width. The sling may be rectangular, as illustrated in the figures, or have another suitable shape. The sling may have a uniform thickness over the entire length and/or width of sling, or the thickness may vary at one or more locations. According to the illustrative embodiment, the thickness of the sling material ranges from about 0.002 mm to about 5.0 mm. The sling used with the invention is a strip of mesh with any of a number and configurations of knits, weaves or braids, and is sized and shaped for placement in the periurethral tissues of a patient to provide a urethral platform to treat urinary incontinence.

The sling used with the invention may be fabricated from any of a number of biocompatible materials, such as nylon, polyethylene, polyester, polypropylene, fluoropolymers, copolymers thereof, combinations thereof, or other suitable synthetic material(s). The sling material may be fabricated from one or more yarns, which yarns may be made from one or more materials. The sling may incorporate or be coated with one or more agents to provide a therapeutic effect, for example, to reduce discomfort, to reduce the chance of infection and/or to promote tissue growth. The sling material may also be made of a combination of mammalian tissue and synthetic material(s).

The edge regions of the sling used with the invention can be configured differently depending on their intended placement in the body of the patient. For example, a middle section of the sling is typically located where an anatomical site, such as a midurethral or bladder neck location in the periurethral tissue, needs to be supported. In one illustrative embodiment, the middle portion of the sling assembly, including the section around the second end 102b of the first sling section 102 and the section around the first end 104a of the second sling section 104, has smooth or rounded edges, hereinafter also referred to as "non-tanged." According to a further illustrative embodiment, other sections of the sling may include tangs (e.g., sharp projections or frayed edges). The tangs are generally useful for anchoring the sling and encouraging tissue growth into the sling. Anchoring the sling in this manner generally obviates the need for additional sutures to hold the sling in place. Anchoring the sling via its tangs is especially useful for anchoring the sling on a tissue and facilitating the removal of the sleeve according to the invention by pulling on the center tab of the sleeve while the sling stays in place, without the need for additional incisions in order to hold the sling external to the body while the sleeve is being removed through pulling.

The tanged and non-tanged edges of the sling may be formed in a plurality of ways. For example, the sling can be cut from a woven sheet, in which case the edges would be initially tanged along the entire length of the sling. One or more non-tanged sections may be formed by any process that smoothes, rounds or removes the sharp edges of the tangs. For example, the tangs may be heat-smoothed by burning or melting the tangs. In one embodiment, the non-tanged section has a length of about 1 cm to about 5 cm, preferably about 2 cm to about 2.5 cm, on either or both sides of the center of the sling. Providing one or more non-tanged sections, which may be in close proximity to a sensitive anatomical site in the patient, can enhance the comfort level of the patient and reduce the potential for the edges of the tangs to erode or irritate the urethra. Alternatively, the sling can be produced from a woven tape having the approximate finished width of the sling. The smooth sides of the tape can then be trimmed off to produce the tanged sections.

The sling assembly of the invention may be delivered by enclosing the sling assembly in a protective sleeve during the placement procedure. Once the sling assembly is correctly positioned in the patient's periurethral tissues, the sleeve is physically removed from about or slid off the sling and withdrawn from the patient's body, leaving behind the sling in the patient's tissues. Alternatively, the sling assembly of the invention may include a biocompatible dissolvable protective treatment that covers at least a portion of the sling assembly, thus eliminating the need for a protective sleeve during placement of the sling. Such protective treatment is described in the co-pending U.S. application Ser. No. 11/098,178 filed Apr. 4, 2005, entitled "Dissolvable Protective Treatment for an Implantable Supportive Sling," the entire contents of which are incorporated herein by reference.

According to another illustrative feature, the biodegradable connection mechanism and/or the sling may also include an agent for release into the patient's tissues. One illustrative agent is a tissue growth factor that promotes, when applied to the patient's tissues in a pharmaceutically acceptable amount, well-organized collagenous tissue growth, such as scar tissue growth, preferably, in large quantities. According to one feature, the agent may or may not block or delay the dissolvability of the biodegradable materials. This may be controlled by selecting differing methods for loading the agent onto the sling. The tissue growth factor may include natural and/or recombinant proteins for stimulating a tissue response so that collagenous tissue such as scar tissue growth is enhanced. Exemplary growth factors that may be used include, but are not limited to, platelet-derived growth factor (PDGF), fibroblast growth factor (FGF), transforming growth factor-beta (TGF-beta), vascular endothelium growth factor (VEGF), Activin/TGF and sex steroid, bone marrow growth factor, growth hormone, Insulin-like growth factor 1, and combinations thereof. The agent may also include a hormone, including but not limited to estrogen, steroid hormones, and other hormones to promote growth of appropriate collagenous tissue such as scar tissue. The agent may also include stem cells or other suitable cells derived from the host patient. These cells may be fibroblast, myoblast, or other progenitor cells to mature into appropriate tissues.

In various illustrative embodiments, the agent may include one or more therapeutic agents. The therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof.

Exemplary steroidal anti-inflammatory therapeutic agents (glucocorticoids) include, but are not limited to, 21-acetoxypreffenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Exemplary non-steroidal anti-inflammatory therapeutic agents include, but are not limited to, aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, aldofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid; carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as ϵ-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Exemplary narcotic analgesic therapeutic agents include, but are not limited to, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Exemplary non-narcotic analgesic agents that may be combined with the slings of the invention include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Exemplary local anesthetic therapeutic agents include, but are not limited to, ambucaine, amolanone, amylocalne hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Exemplary antispasmodic therapeutic agents include, but are not limited to, alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-ltrimethyl-3,3-diphenylpropylamine, tropenzile, trospium chloride, xenytropium bromide, and pharmaceutically acceptable salts thereof.

The agent may be associated with the biodegradable connection mechanism and/or the sling in a variety of manners. For example, the agent may be chemically or physically attached to the surface of one or more of the fibers of the sling or to the surface of the biodegradable connection mechanism. In one illustrative embodiment, the surface of the sling and/or the biodegradable connection mechanism and the agent, for example, in solution, have complementary ionic charges. As such, when placed on the sling and/or the biodegradable connection mechanism, the agent ionically bonds to its surface. According to the invention, any suitable process may be employed for associating the agent with the sling and/or the biodegradable connection mechanism, such that the agent can leach to tissue in the region of the implanted sling and the biodegradable connection mechanism can dissolve into the bodily fluids or leach into the tissue in the region of the implanted sling.

In an exemplary method of treating urinary incontinence using the invention, a medical operator places the sling assembly in the periurethral tissue of a patient adjacent to the patient's urethra by any suitable approach, such as any of those mentioned above. Illustratively, the medical operator introduces a shaft having a first end of the sling assembly associated therewith into the patient's body transvaginally at a first site on a first side of the urethra, and causes the distal end of the shaft to emerge from the patient's abdominal wall. The operator then grasps and stabilizes the first end of the sling assembly and backs the shaft out of the patients body. The operator then repeats the process on the contralateral side of the patients body for the second end of the sling assembly.

In alternative embodiments, rather than using a transvaginal approach as described above, the operator approaches the patient's periurethral tissues using a supra-pubic approach (e.g., percutaneously through the abdominal wall, abdominal fascia, and rectus fascia), a transobtural approach (e.g., around the ischiopubic ramus percutaneously through the obturator membrane and periurethral endopelvic fascia to a vaginal incision or from a vaginal incision through the periurethral endopelvic facia and obturator membrane and out around the ischiopubic ramus), or a pre-pubic approach (e.g., from the abdominal wall along the anterior surface of the pubic bone).

As described above, the tension-adjustable sling assembly described herein may be delivered to an anatomical site in a patient's body by way of any suitable delivery device or delivery approach, including by way of an abdominal (e.g., supra-pubic), transvaginal, transobtural, or pre-pubic approach. Also, the sling or sling assembly may employ any suitable sling assembly-to-delivery device association mechanism. Once implanted, the sling may employ any suitable anchoring mechanism or none at all.

Without limitation, examples slings, sling assemblies, sling delivery devices and approaches, sling assembly-to-delivery device association mechanisms, and sling anchoring mechanisms with which the invention may be employed disclosed in U.S. Pat. No. 6,042,534, entitled "Stabilization sling for use in minimally invasive pelvic surgery," U.S. Pat. No. 6,755,781, entitled "Medical slings," U.S. Pat. No. 6,666,817, entitled "Expandable surgical implants and methods of using them," U.S. Pat. No. 6,042,592, entitled "Thin soft tissue surgical support mesh," U.S. Pat. No. 6,375,662, entitled "Thin soft tissue surgical support mesh," U.S. Pat. No. 6,669,706, entitled "Thin soft tissue surgical support mesh," U.S. Pat. No. 6,752,814, entitled "Devices for minimally invasive pelvic surgery," U.S. patent application Ser. No. 10/918,123, entitled "Surgical Slings," U.S. patent application Ser. No. 10/641,376, entitled "Spacer for sling delivery system," U.S. patent application Ser. No. 10/641,192, entitled "Medical slings," U.S. Ser. No. 10/641,170, entitled "Medical slings," U.S. Ser. No. 10/640,838, entitled "Medical implant," U.S. patent application Ser. No. 10/460,112, entitled "Medical slings," U.S. patent application Ser. No. 10/631,364, entitled "Bioabsorbable casing for surgical sling assembly," U.S. Ser. No. 10/092,872, entitled "Medical slings," U.S. patent application Ser. No. 10/939,191, entitled "Devices for minimally invasive pelvic surgery," U.S. patent application Ser. No. 10/774,842, entitled "Devices for minimally invasive pelvic surgery," U.S. patent application Ser. No. 10/774,826, entitled "Devices for minimally invasive pelvic surgery," U.S. Ser. No. 10/015,114, entitled "Devices for minimally invasive pelvic surgery," U.S. patent application Ser. No. 10/973,010, entitled "Systems and methods for sling delivery and placement," U.S. patent application Ser. No. 10/957,926, entitled "Systems and methods for delivering a medical implant to an anatomical location in a patient," U.S. patent application Ser. No. 10/939,191, entitled "Devices for minimally invasive pelvic surgery," U.S. patent application Ser. No. 10/918,123, entitled "Surgical slings," U.S. patent application Ser. No. 10/832,653, entitled "Systems and methods for sling delivery and placement," U.S. patent application Ser. No. 10/642,397, entitled "Systems, methods and devices relating to delivery of medical implants," U.S. patent application Ser. No. 10/642,395, entitled "Systems, methods and devices relating to delivery of medical implants," U.S. patent application Ser. No. 10/642,365, entitled "Systems, methods and devices relating to delivery of medical implants," U.S. patent application Ser. No. 10/641,487, entitled "Systems, methods and devices relating to delivery of medical implants," U.S. patent application Ser. No. 10/094,352, entitled "System for implanting an implant and method thereof," U.S. patent application Ser. No. 10/093,498, entitled "System for implanting an implant and method thereof," U.S. patent application Ser. No. 10/093,450, entitled "System for implanting an implant and method thereof," U.S. patent application Ser. No. 10/093,424, entitled "System for implanting an implant and method thereof," U.S. patent application Ser. No. 10/093,398, entitled "System for implanting an implant and method thereof," U.S. patent application Ser. No. 10/093,371, entitled "System for implanting an implant and method thereof," U.S. Provisional Application No. 60/569,300, entitled "Systems and methods for delivering a medical implant to an anatomical location in a patient," and U.S. Provisional Application No. 60/508,600 entitled "Systems and methods for delivering a medical implant to an anatomical location in a patient," the entire contents of all of which are incorporated herein by reference.

What is claimed is:

1. A sling assembly for treating urinary incontinence comprising:
    first and second separate and distinct mesh sling sections, each mesh sling section having first and second terminal ends and first and second sides extending from the first terminal end to the second terminal end, a distance between the first and second terminal ends defining a length of each mesh sling section, a distance between the first and second sides defining a width of each mesh sling section, the first and second mesh sling sections being non-biodegradable; and
    a rod interfitted with the second terminal end of the first mesh sling section and the first terminal end of the second mesh sling section to connect the first and the second mesh sling sections in series with the second terminal end of the first mesh sling section overlapping and in contact with the first terminal end of the second mesh sling section, the rod being interwoven through the overlapping portion of the first mesh sling section and the second mesh sling section such that the rod extends an entire width of the first and second mesh sling sections, the rod being biodegradable such that the rod dissolves over time to separate the first and second mesh sling sections.

2. The sling assembly of claim 1, wherein the rod includes an agent that promotes organized scar tissue formation.

3. The sling assembly of claim 1, wherein the rod is a biodegradable polymer.

4. The sling assembly of claim 1, wherein the rod includes polylactic acid (PLA).

5. The sling assembly of claim 1, wherein the length of each mesh sling section is between 10 cm and 45 cm, and the width of each mesh sling section is between 0.5 cm and 5.5 cm.

6. The sling assembly of claim 1, wherein each mesh sling section has a uniform thickness over the length and the width of each mesh sling section.

7. The sling assembly of claim 1, wherein an agent is coupled to the rod such that a dissolvability of the rod is delayed.

* * * * *